United States Patent
Majeed et al.

(10) Patent No.: US 6,982,273 B1
(45) Date of Patent: Jan. 3, 2006

(54) COMPOSITIONS AND METHODS CONTAINING BIOAVAILABLE SE-METHYL-L-SELENOCYSTEINE FOR HUMAN AND VETERINARY USE

(75) Inventors: Muhammed Majeed, Piscataway, NJ (US); Nagarajan Ananthanarayanan, Bangalore (IN); Nagabhushanam Kalyanam, Piscataway, NJ (US); Ramanujam Rajendran, Bangalore (IN); Seena George, Bangalore (IN); Subbalakshmi Prakash, Piscataway, NJ (US)

(73) Assignee: Sami Labs Ltd., Bangalore (IN)

( * ) Notice: Subject to any disclaimer, the term of this patent is extended or adjusted under 35 U.S.C. 154(b) by 0 days.

(21) Appl. No.: 10/707,716

(22) Filed: Jan. 6, 2004

Related U.S. Application Data

(63) Continuation-in-part of application No. 10/065,677, filed on Nov. 7, 2002, now Pat. No. 6,794,537.

(51) Int. Cl.
*A61K 31/445* (2006.01)
(52) U.S. Cl. .................................................. 514/321
(58) Field of Classification Search ............... 514/561; 562/557
See application file for complete search history.

(56) References Cited

PUBLICATIONS

Andreadou et al Journal of Medicinal Chemistry 1996, 39(10), pp. 2040-2046.*

* cited by examiner

*Primary Examiner*—Paul A. Zucker

(57) ABSTRACT

The invention discloses compositions containing Se-methyl-L-selenocysteine with enhanced bioavailability and superior antioxidant and immunomodulatory activity. These compositions can be used for nutritional supplementation in humans and animals.

1 Claim, 6 Drawing Sheets

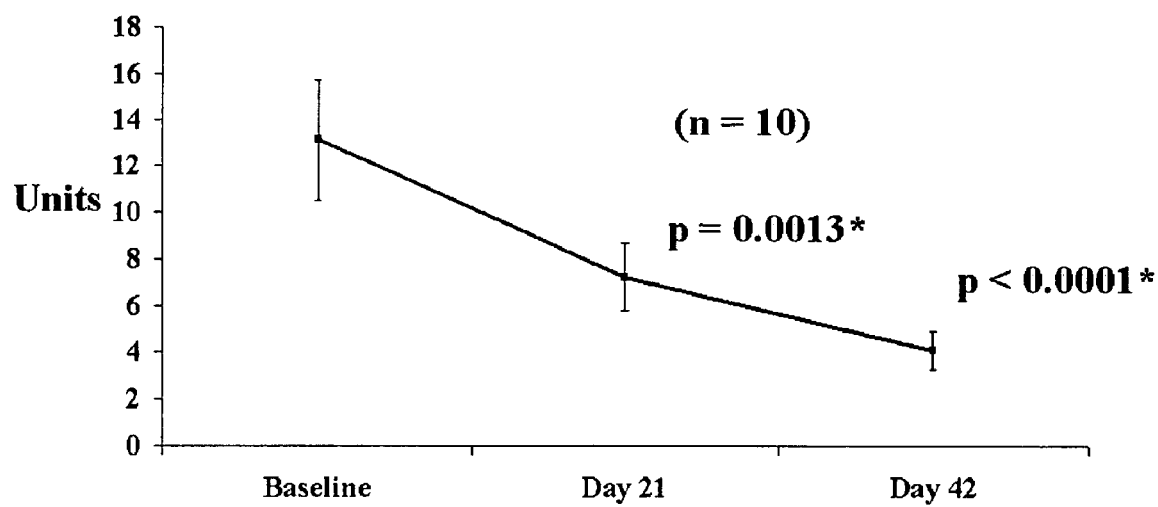
Figure 1: Plasma Lipid Peroxidation

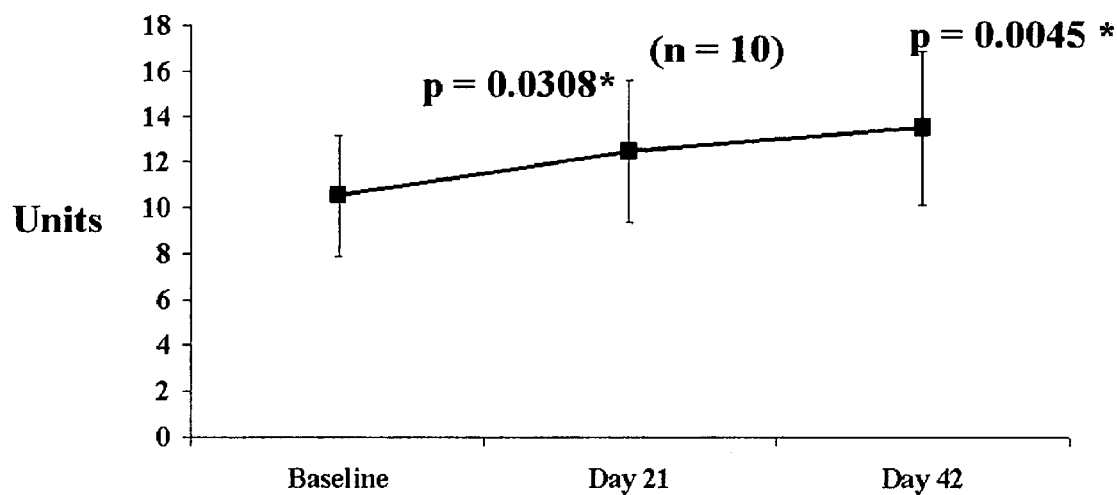
Figure 2: Glutathione S-transferase

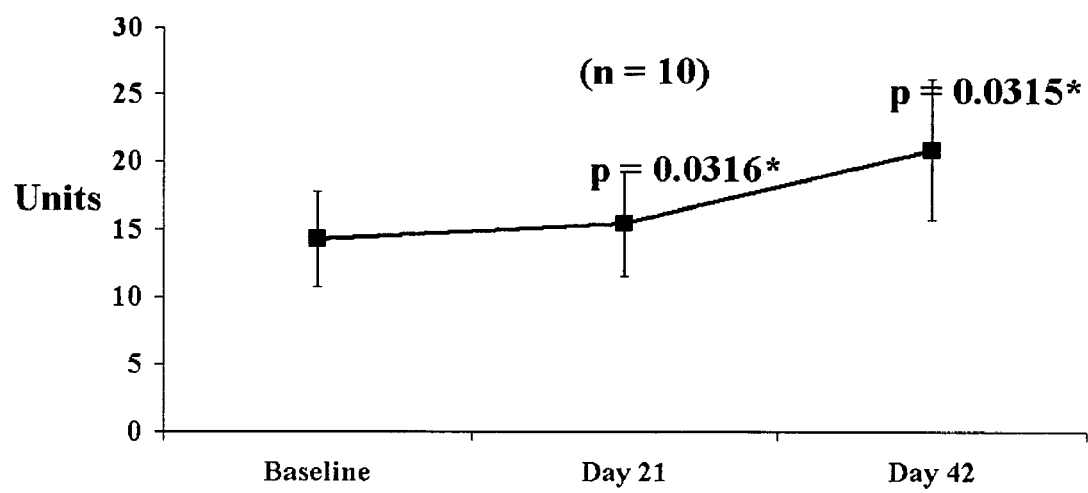
Figure 3: Superoxide Dismutase

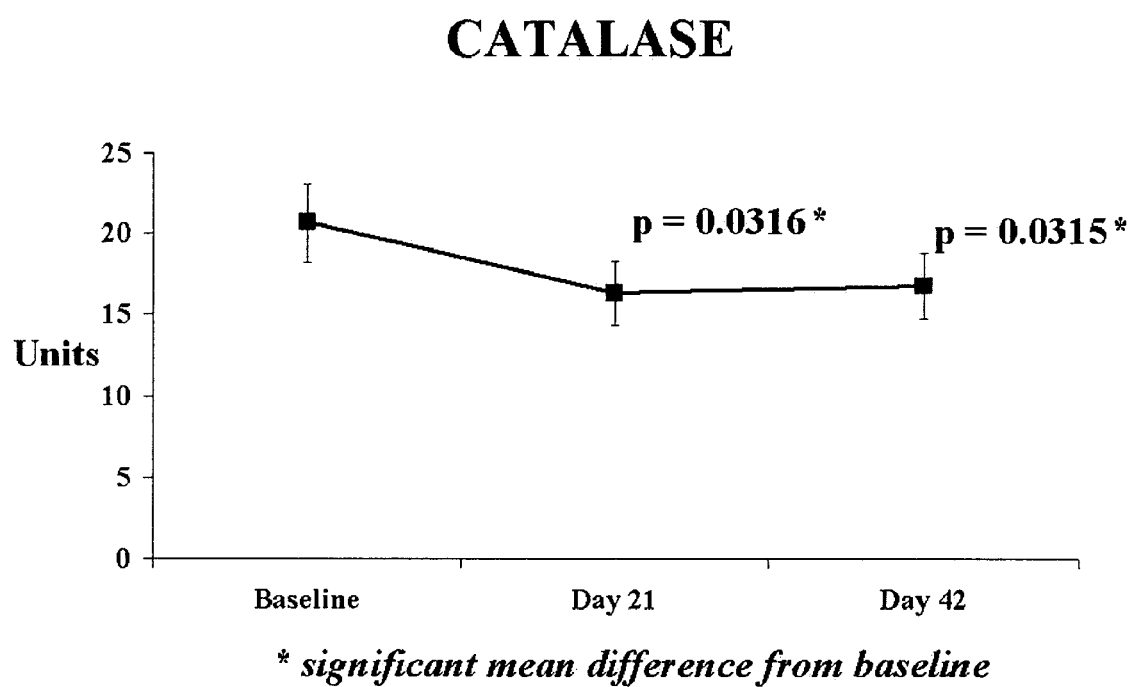
Figure 4: Catalase

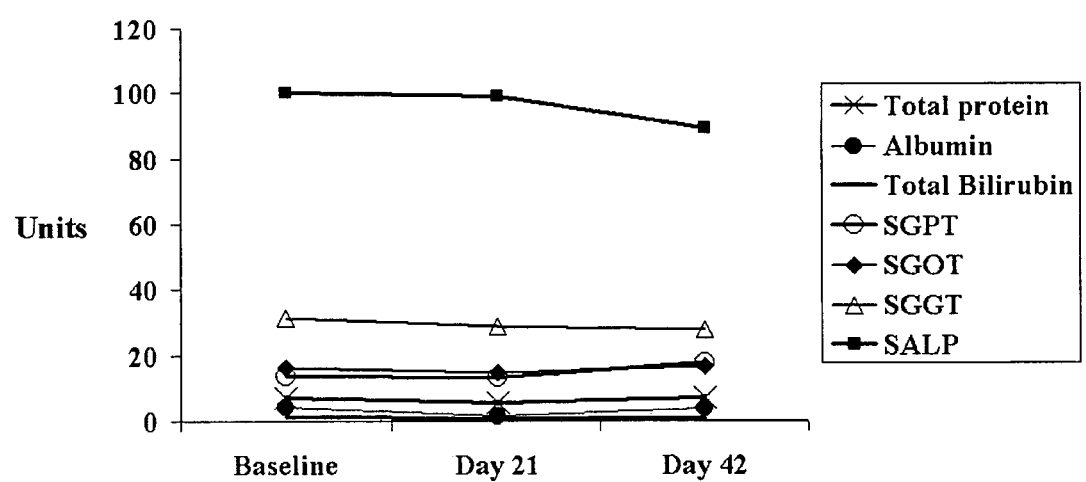
Figure 5: Liver Function Parameters

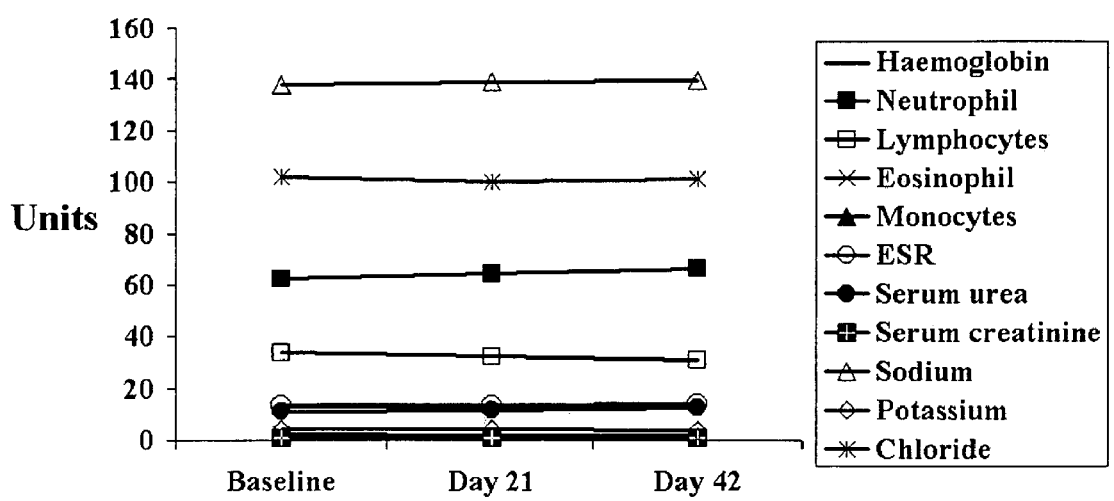
Figure 6: Kidney Function Parameters

COMPOSITIONS AND METHODS CONTAINING BIOAVAILABLE SE-METHYL-L-SELENOCYSTEINE FOR HUMAN AND VETERINARY USE

CROSS REFERENCE TO RELATED APPLICATIONS

This application is a continuation-in-part of U.S. patent application Ser. No. 10/065,677 filed on Nov. 7, 2002, now U.S. Pat. No. 6,794,537 titled manufacturing processes for Se-methyl L-selenocysteine, the disclosure of which is hereby incorporated by reference.

BACKGROUND OF INVENTION

The present invention is related to compositions and methods containing Se-methyl-L-selenocysteine, and the use of these compositions to provide health benefits in animals and humans.

The parent application disclosed novel processes for preparing Se-alkylselenocysteine, Se-allylselenocysteine, Se-arylselenocysteine. The current invention provides compositions containing Se-methyl-L-selenocysteine with enhanced bioavailability, for nutritional supplementation and pharmaceutical use in humans and animals. The bioavailability is enhanced by the addition of black pepper extract (standardized to contain 95–98% piperine).

Selenium is a vital trace element nutrient with multiple roles in the growth and functioning of living cells in higher animals and humans. At the molecular level, selenium (as selenocysteine) is an essential component of the active sites of the antioxidant enzyme glutathione peroxidase, and the enzymes participating in thyroid functions iodothyronine-5'-deiodinase and mammalian thioredoxin reductase. Selenium is also present in several other mammalian selenoproteins. Low selenium status has been linked with the occurrence of decreased immunity to diseases and the prevalence of various forms of cancer.

Selenium occurs in foods, through uptake by plants from the soil, in the form of the selenoamino acids, selenomethionine and selenocysteine, and their derivatives. However, as the element is unevenly distributed in the earth's crust, dietary supplementation is often needed. Organic selenium compounds are preferred for supplementation on account of their superior bioavailability. An ideal nutritional supplement would be a selenium enriched edible plant part wherein the selenium metabolically accumulates in the form of bioavailable organic selenium compounds. Plants that naturally contain higher levels of the sulfur containing amino acids such as those from the *Allium* and *Brassica* species are preferred for enrichment, based on metabolic criteria. Selenium-enriched garlic is reported to be useful as a nutritional supplement in the prevention of cancer (Ip, et al., 1992, 1996; Ip and Lisk, 1993, 1997; Lu et al., 1996).

Clinical intervention trials and in vitro data revealed the efficacy of selenium in the form of selenium yeast or selenomethionine in cancer prevention (Clark et al., 1996, 1998). Ip et al (2000) described the role of chemical speciation on the comparative activity of selenium-enriched garlic and selenium yeast in mammary cancer prevention in rats, wherein selenium-enriched garlic was shown to be more efficacious than selenium yeast. γ-glutamyl Se-methylselenocysteine is reported to be the major form of selenium in selenium-enriched garlic while L-Selenomethionine was shown to be the major form of selenium in selenium enriched yeast.

Laboratory studies indicate that γ-Glutamyl-Se-methyl-L-selenosysteine is an effective chemopreventive agent, serving as a carrier for Se-Methyl-L-selenocysteine (Dong et al., 2001; Medina et al., 2001). Se-Methyl-L-selenocysteine is a well researched chemopreventive organoselenium compound, which is not incorporated in the body proteins, and is therefore less toxic than other forms of supplemental selenium (Ip et al., 1994; Medina et al., 2001).

A study that compared the chemopreventive activities of selenium compounds, in the rat dimethyl-benz(a)anthracene-induced mammary tumor model reported that 1–2 ppm Se in the diet of rats 1 week before dimethylbenz(a) anthracene administration and continuing until sacrifice, resulted in tumor inhibition. The efficacy of the selenium compounds was in the following order: Se-methylselenocysteine greater than selenite greater than selenocysteine greater than dimethyl selenoxide (Ip et al., 1991).

In a bioavailability study using Se-methylselenocysteine, dimethyl selenoxide, and trimethylselenonium as the starting compounds for delivering selenium with one, two, or three methyl groups, researchers measured the ability of these compounds to restore glutathione peroxidase activity in selenium-depleted animals. All three compounds were able to fully replete this enzyme, although with a wide range of efficiency (Se-methylselenocysteine greater than dimethyl selenoxide greater than trimethylselenonium). (Ip et al., 1991).

Spallholz, J. E.; Reid, T. W.; Walkup, R. D. described a method of using synthetic L-Se-methylselenocysteine as a nutraceutical and a method of its synthesis, EP 1 205 471, 2001 and U.S. 20030083383 A1. They claim the health benefits of Se-methyl-L-selenocysteine as a nutritional supplement in humans and animals.

U.S. Pat. Nos. 5,536,506, 5,744,161, 5,972,382, 6,054,585 by Majeed, et al. describe the use of black pepper extract containing 95–98% piperine to enhance the bioavailability of several nutritional compounds and herbal extracts.

The parent application disclosed novel methods for the synthesis of Se-methyl-L-selenocysteine and related compounds. The method of the current invention permits the utilization of lower amounts of Se-methyl-L-selenocysteine in formulations with enhanced efficacy, and lowered risk of selenium toxicity.

The composition also effectively suppresses liver injury indicating superior antioxidant and anti-inflammatory effects. Selenium compounds for example Ebselen are reported to inhibit macrophage induced liver injury (Koyanagi, wt al. 2001).

The composition is also useful in autoimmune disorders such as psoriasis. Selenium nutritional status is reported to be insufficient in patients with long term psoriasis (Harvima, 1993).

The following is a list of literature cited in this application, each of which is hereby incorporated by reference in its entirety:

1. Ip, C., Lisk, D. J, and Stoewsand, G. S. 1992. "Mammary Cancer prevention by Regular Garlic and Selenium-Enriched Garlic." Nutr. Cancer 17, 279–286.
2. Ip. C, and Lisk, D. J. 1996. "The attributes of Selenium_Enriched Garlic in Cancer Prevention." In Dietary Phytochemicals in Cancer Prevention and Treatment 15, 179–187.

3. Ip. C, and Lisk, D. J. 1993. "Bioavailability of Selenium From SeleniumEnriched Garlic." Nutr. Cancer 20, 129–137.
4. Ip, C and Lisk, D. J. 1997. "Modulation of phase I and Phase II Xenobiotic-metabolizing Enzymes by Enriched Garlic in rats." Nutr. and Cancer 28(2), 184–188.
5. Lu., J., Pei H., Ip C., Lisk D J., Ganther H and Thompson H J., 1996. Effect on an aqueous extract of selenium enriched garlic on in vitro and in vivo efficacy in cancer prevention. Carcinogenesis,17(9): 1903 1907.
6. Ip, C; Ganther, H. Novel Strategies In Selenium Cancer Chemoprevention Research; In Selenium In Biology and Human Health; Burk, R. F. Ed; (1994) Springer-Verlag, New York: 169 180.
7. Ip. C., et al. 2000. Chemical Speciation Influences Comparative Activity of Selenium-Enriched Garlic and Yeast in Mammary Cancer Prevention. J. Agric. Food Chem. 48, 2062–2070
8. Dong, Y. et al. 2001 Characterization and Biological Activity of γ-Glutamyl-Se Methylselenocysteine: A Novel, Naturally Occurring Anticancer Agent From Garlic. Cancer Res. 61:2923–2928.
9. Medina, D. et al. 2001 Se-Methylselenocysteine: A new compound for chemoprevention of breast cancer. Nutrition and Cancer 40(1):12–17.
10. Clark L C, et al. 1996 Effects of selenium supplementation for cancer prevention in patients with carcinoma of the skin. A randomized controlled trial. Nutritional Prevention of Cancer Study Group. JAMA. 276(24):1957–63.
11. Clark, L C et al. 1998 Inhibitory effect of selenomethionine on the growth of three selected human tumor cell lines. Cancer Lett.; 125(1–2):103–10.
12. Ip, C., et al. 1991. Chemical form of selenium, critical metabolites, and cancer prevention. Cancer Res.; 51(2): 595–600.
13. Koyanagi, T. et al. 2001 The selenoorganic compound ebselen suppresses liver injury induced by Propionibacterium acnes and lipopolysaccharide in rats. Int. J. Mol. Med. 7(3): 321–327.
14. Harvima, R. J. (1993) Screening of effects of selenomethionine-enriched yeast supplementation on various immunological and chemical parameters of skin and blood in psoriatic patients. Acta Derm. Venerol. 73(2): 88–91.

SUMMARY OF INVENTION

The current invention provides compositions containing Se-methyl-L-selenocysteine with enhanced bioavailability for nutritional supplementation in humans and animals. The bioavailability is enhanced by the addition of black pepper extract (standardized to contain 95–98% piperine). The compositions provide a safe and efficacious means of providing supplemental amounts of the essential trace mineral nutrient selenium for diverse health benefits. Toxicological studies revealed that the $LD_{50}$ of the compositions in rats is greater than 8.8 mg/kg body weight.

Supplementation with the composition of the invention produced positive improvement in antioxidant profile in human subjects with no adverse effects. Antioxidant profile refers to the levels of lipid oxidation products (lipid peroxides) and the levels of protective antioxidant enzymes (Glutathione-S— transferase, Superoxide dismutase and Catalase) in the plasma of the subjects. Glutathione S-transferase (GST) is a key detoxicant enzyme that removes toxic substances in the body, through conjugation with glutathione or reduction by glutathione peroxidase.

BRIEF DESCRIPTION OF DRAWINGS

FIG. 1 shows the effects of supplementation with the composition on plasma lipid peroxidation in human subjects.

FIG. 2 shows the effects of supplementation with the composition on glutathione peroxidase levels in human subjects.

FIG. 3 shows the effects of supplementation with the composition on superoxide dismutase activity in human subjects.

FIG. 4 shows the effects of supplementation with the composition on catalase activity in human subjects.

FIG. 5 shows that supplementation with the composition for 42 days produced no adverse effects on liver function parameters in human subjects.

FIG. 6 shows that supplementation with the composition for 42 days produced no adverse effects on kidney function parameters in human subjects

DETAILED DESCRIPTION

The invention discloses compositions containing Se-methyl-L-selenocysteine with enhanced bioavailability and superior antioxidant and immunomodulatory activity.

EXAMPLE 1

Efficacy of the composition in suppressing macrophage induced liver injury

Study objective: To determine whether the composition of the invention shows superior efficacy and safety in suppressing macrophage associated liver injury and endotoxemia in rats. The composition used consisted of Se-methyl-L-selenocysteine of the parent application to which piperine from black pepper fruit was added such that the animals received a co-administered daily dose of 5 mg of piperine.

Study Design: Male Wistar King A rats (200–250 g) were maintained on a basal pelleted diet and water ad libitum under normal temperature and lighting conditions. All rats received an injection of 40 mg/kg body weight of heat killed *Propionibacterium acnes* (ATCC 11827), 20 mg/ml suspension in saline via the tail vein on day 1. Seven days later they received an intravenous injection of 350 mcg/kg body weight of lipopolysaccharide (LPS, Difco Laboratories, MI, USA), 200 mcg/ml solution in saline). 5 rats received a daily dose of 4 mg/kg body weight of Se-methyl-L-selenocysteine and 5 rats received 2 mg/kg body weight of the composition of the invention, orally for 3 days in the feed, 4 control rats received no supplementation, prior to induction of liver injury, 4 normal controls were not subjected to liver injury. Serum levels of TNF-α were measured. TNF-α is thought to be the principal mediator of the deleterious effects of LPS. Serum levels of lipid peroxides and antioxidant enzymes were also measured The results are shown in Table 1

TABLE 1

Effects of the composition on biochemical parameters in rats with macrophage associated liver injury and endotoxemia.

| Parameter | Treatment | | | |
|---|---|---|---|---|
| | Control (normal) (n = 4) | Control (*P. acnes* + LPS) (n = 4) | Se-methyl-L-selenocysteine Treated (n = 5) | Composition of the invention Treated (n = 5) |
| Survival rate | | 1/4 | 3/5 | 5/5 |
| TNF-alpha | 40 ± 3 | 92 ± 4 ng/ml | 81 ± 6 ng/ml | 55 ± 4 ng/ml** |
| Serum Lipid peroxides (MDA formed/mg protein) | 2.35 ± 0.21 | 3.83 ± 0.33 | 2.71 ± 0.32 | 2.59 ± 0.25** |
| Superoxide dismutase (Units/min/mg protein) | 5.62 ± 0.46 | 3.97 ± 0.41 | 4.91 ± 0.48 | 5.57 ± 0.50** |
| Catalase micromole of $H_2O_2$ consumed/min/mg protein) | 47.12 ± 4.30 | 22.16 ± 2.07 | 31.16 ± 3.95 | 45.07 ± 4.23** |
| Glutathione peroxidase (micromole of GSH oxidized/min/mg protein) | 9.23 ± 0.82 | 5.78 ± 0.53 | 8.13 ± 0.71 | 9.08 ± 0.85** |
| Glutathione (GSH) mcg/mg protein | 8.65 ± 0.72 | 6.16 ± 0.56 | 7.43 ± 0.69 | 8.24 ± 0.65** |

**significant p < 0.05 as compared to (*P. acnes* + LPS) control

EXAMPLE 2

Clinical efficacy and safety of the composition

Study Objective: To determine the efficacy and safety of the composition in reducing oxidative stress levels in humans.

Composition used: Each tablet provided 100 mcg of elemental selenium derived from Se-methyl-L-selenocysteine of the parent application in combination with 5 mg of piperine from black pepper fruit.

Study Design: 42-day open prospective single centre study to measure the efficacy and safety of composition. In this 42 day study, each patient was administered the composition (providing 100 mcg of selenium) in a single dose, daily after a meal. Selection of Subjects: The selection criteria stipulated were that the subjects have a BMI (body mass index) of 20–38 kg/m2, fall in the age group of 35 to 60 years, with an increased risk of heart disease. These subjects would be otherwise in good health, with no history of alcohol or drug abuse, and no known allergies. Kidney and liver functions would be normal. 13 subjects (in the age group of 25 to 43 years (6 males and 7 females)), participated in the study.

Study Procedures: Efficacy was assessed based on change in oxidative stress, as evidenced by measuring antioxidant profile. Safety was assessed based on standard liver function and kidney function tests. Adverse events, if any, were recorded. Liver function is assessed by using specific enzyme markers. For example, both SGPT (Serum Glutamate-Pyruvate Transaminase) and SGOT (Serum Glutamate-Oxaloacetate Transaminase) are important in the clinical diagnosis of disease. These enzymes, particularly abundant in heart and in liver, are released from injured cells in myocardial infarction, infections, liver damage or cardiovascular disease. Kidney function tests seek to evaluate how well the kidneys filter and transport metabolic waste from the blood into the urine. Serum creatinine, serum urea, and electrolyte (sodium, potassium and chloride) levels are measured. ESR (Erythrocyte sedimentation Rate) and haemoglobin levels, if abnormal, provide an indication of the presence of disease.

Results: Efficacy: From day 0 (baseline) to day 21, and from day 0 to day 42, plasma lipid peroxidation reduced by an average of 5.39 units and 9.28 units respectively. Both decreases were statistically significant (FIG. 1). Lymphocyte antioxidant count for Glutathione-S-transferase and Superoxide dismutase were found to increase from day 0 to day 21, and from day 0 to day 42. The Catalase values decreased during this period. All the mean differences from baseline were found to be statistically significant (FIGS. 2–4).

Safety: The laboratory values of parameters for liver function and kidney function were found to be within admissible limits, with minor changes reported during the course of the study. The variation was within 5% of normal values (FIGS. 5 and 6). Similarly blood lipid profiles remained within the normal range. No adverse events were observed in any of the subjects or reported during the study.

Conclusions: The results of this open prospective clinical study suggest that the composition effectively reduces oxidative stress levels, and is safe for use as an antioxidant nutritional supplement.

While an exemplary embodiment of the composition and its use is presented in the current invention, the intention is to cover all modifications and alterations falling within the scope of the appended claims.

What is claimed is:

1. A bioavailable nutritional supplement composition comprising Se-methyl-L-selenocysteine combined with black pepper extract standardized to contain 95–98% piperine.

* * * * *